United States Patent [19]
Yui et al.

[11] Patent Number: 5,374,375
[45] Date of Patent: Dec. 20, 1994

[54] LIQUID CRYSTAL COMPOUND AND LIQUID CRYSTAL DISPLAY DEVICE

[75] Inventors: Tomoyuki Yui, Nagareyama; Masahiro Johno, Tsukuba; Toshio Watanabe, Tsukuba; Masamichi Mizukami, Tsukauba; Yoshihisa Arai, Tsukuba, all of Japan

[73] Assignee: Mitsubishi Gas Chemical Co., Inc., Tokyo, Japan

[21] Appl. No.: 905,193

[22] Filed: Jun. 26, 1992

Related U.S. Application Data

[63] Continuation of Ser. No. 678,937, Apr. 3, 1991, abandoned.

[30] Foreign Application Priority Data

| Apr. 4, 1990 | [JP] | Japan | 2-88180 |
| Apr. 11, 1990 | [JP] | Japan | 2-94053 |
| Aug. 27, 1990 | [JP] | Japan | 2-222543 |

[51] Int. Cl.$^5$ .................. C09K 19/12; C09K 19/52; C07C 69/76
[52] U.S. Cl. .................. 252/299.65; 560/102; 252/299.66
[58] Field of Search .................. 252/299.65; 560/102

[56] References Cited
U.S. PATENT DOCUMENTS

| 4,596,667 | 6/1986 | Inukai et al. | 252/299.65 |
| 4,647,398 | 3/1987 | Saito et al. | 252/299.65 |
| 4,668,427 | 5/1987 | Saito et al. | 252/299.66 |
| 4,914,224 | 4/1990 | Shoji et al. | 560/65 |
| 4,943,386 | 7/1990 | Takehara et al. | 252/299.65 |
| 5,078,477 | 1/1992 | Jono et al. | 359/91 |
| 5,108,650 | 4/1992 | Koden et al. | 252/299.01 |
| 5,116,531 | 5/1992 | Hagiwara et al. | 252/299.65 |
| 5,155,611 | 10/1992 | Yamazaki et al. | 359/76 |
| 5,171,471 | 12/1992 | Suzuki et al. | 252/299.61 |
| 5,202,054 | 4/1993 | Suzuki et al. | 252/299.61 |

FOREIGN PATENT DOCUMENTS

| 0342046 | 11/1989 | European Pat. Off. |
| 60-32748 | 7/1983 | Japan |
| 63-33351 | 7/1986 | Japan |
| 63-201147 | 2/1987 | Japan |

OTHER PUBLICATIONS

Chemical Abstracts 112: 207693e.
Chemical Abstracts 112: 149976m.
Chemical Abstract 111(22) 2071962.

Primary Examiner—Robert L. Stoll
Assistant Examiner—C. Harris
Attorney, Agent, or Firm—Sherman and Shalloway

[57] ABSTRACT

A liquid crystal compound represented by formula (I),

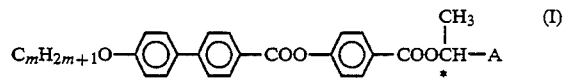

wherein A represents —$C_3H_7$, —$C_4H_9$ or —$C_8H_{17}$; when A is —$C_3H_7$, m is an integer of 8, 10, 12 or 14; and when A is —$C_4H_9$ or —$C_8H_{17}$, m is an integer of 7 to 14, said compound having an antiferroelectric phase.

7 Claims, 9 Drawing Sheets

APPLIED VOLTAGE (V)

APPLIED VOLTAGE (V)

LIQUID CRYSTAL COMPOUND AND LIQUID CRYSTAL DISPLAY DEVICE

This application is a continuation, of application Ser. No. 07/678,937, filed Apr. 3, 1991, now abandoned.

DETAILED DESCRIPTION OF THE INVENTION

This invention relates to a novel liquid crystalline compound and use thereof. More specifically, this invention relates to a liquid crystal compound having an antiferroelectric phase and use thereof.

DESCRIPTION OF THE PRIOR ART

Liquid crystal display device have been to date used as various small-screen devices because of a low voltage, an electric power consumed is low and thin display is possible. However, as the liquid crystal display devices have recently found use in the fields of information, office automation appliances, television, etc., high-performance, large-sized liquid crystal display having higher resolution and higher display qualities than the ordinary CRT display have been increasingly demanded rapidly.

Nevertheless, so far as the present nematic liquid crystals are used as display devices, even active matrix liquid crystal display devices employed in liquid crystal television sets has difficulty to produce a large screen with low cost owing to intricacy of their production process and their low yields. Meanwhile, simple matrix STN liquid crystal display devices are not necessarily easy to drive the large screen with high quality either, and the response time is not so fast too. Accordingly, at the present stage, the nematic liquid crystal display devices cannot be said to meet the demand for the high-performance, large-sized liquid crystal display.

PROBLEMS THE INVENTION AIMS TO SOLVE

Under the circumstances, liquid crystal display devices using ferroelectric liquid crystal compounds arouse interest as liquid crystal display devices having high-speed response- Surface stabilized ferroelectric liquid crystal (SSFLC) devices reported by N. A. Clark and S. T. Lagerwall are noteworthy in that they have high-speed response and a wide viewing angle that have not ever been provided [N. A. Clark and S. T. Lagerwall, Appl. Phys. Lett. 36(1980) 899].

Switching characteristics of said SSFLC have been studied in detail, and many ferroelectric liquid crystal compounds have been proposed to optimize various properties. Separately, devices of switching mechanism different from SSFLC have been also developed at the same time. Tristable switching of liquid crystal compounds having an antiferroelectric phase (hereinafter referred to as "antiferroelectric liquid crystalline compounds") are one of the new switching mechanisms.

A relationship of an applied voltage and a transmittance given when measuring an optical response hysteresis of antiferroelectric liquid crystal devices (devices using antiferroelectric liquid crystal compounds) is shown in FIG. 1. It is shown that three stable states exist in the optical response hysteresis. D-C-E and I-H-J part correspond to two uniform states (Ur, Ul) of the chiral smectic C phase, and a G-A-B part corresponds to a third state reported by Chandani, et al. (Japanese Journal of Applied Physics, vol. 27, No. 5, p. L729, 1988).

Change in transmittance is described referring to FIG. 1. For instance, when a positive voltage is gradually applied, a transmittance changes along A-B-C-D, As the transmittance is little changed as the voltage increases from 0 (V) to $V_1$ (V), the antiferroelectric liquid crystal device can be said to have a clear threshold as a function of the applied voltage. Next, when the voltage is gradually decreased from this state, transmittance is changed along D-E-F-A. On this occasion as well, transmittance is little changed up to a voltage $V_2$ (V); said device can therefore be said to have a sharp threshold as a function of the applied voltage. Moreover, as the threshold $V_1$ (V) during the increase of the voltage is different from the threshold $V_2$ (V) during the decrease of the voltage, the antiferroelectric liquid crystal device is found to have memory effect. Likewise, when a negative voltage is applied and gradually increased, transmittance is changed along A-G-H-I. When the negative voltage is gradually decreased from that state, it is changed along I-J-K-A. In this course also, sharp thresholds $V_3$ and $V_4$ (V) exist. As $V_3$ and $V_4$ are also different voltages, the device is found to have memory effect.

As stated above, the device using the antiferroelectric liquid crystal compound is characterized by tristable switching, sharp DC threshold and good memory effect. Another great characteristic feature is that a layer structure is easily switched by an electric field. Accordingly, it becomes possible to realize a less defective liquid crystal display device.

The characteristics and main qualities of the antiferroelectric phase are described in the above reports, and Japanese Journal of Applied Physics, vol. 28, No. 7, pp. L1261 & L1265, 1989.

As the antiferroelectric liquid crystal compound, 4-(1-methylheptyloxycarbonyl)phenyl-4'-n-octyloxybiphenyl-4-carboxylate is known for example (refer to the above Japanese Journal of Applied Physics). The structural formula and the phase transition temperature thereof are as follows.

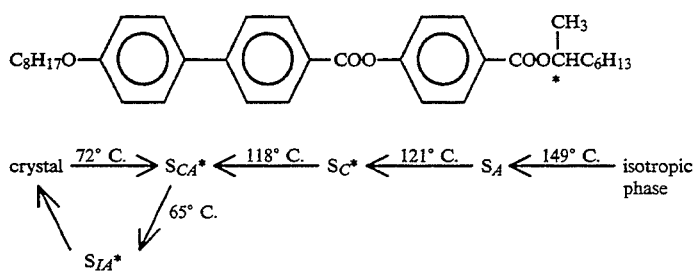

wherein $S_A$, $S_C^*$ $S_{CA}^*$ and $S_A^*$ represent a smectic A phase, a chiral smectic C phase, an antiferroelectric chiral smectic C phase and an antiferroelectic chiral smectic I phase respectively.

As the antiferroelectric liquid crystal compound, those described in Japanese Laid-open Patent Appln. (Kokai) Nos. 213390/1989, 316339/1989, 316367/1989, 316372/1989 and 28128/1990 and Liquid Crystals, vol. 6, No. 2, p. 167, 1989 are known. Mean-while, studies over the antiferroelectric liquid crystal compounds have just started, and antiferroelectric liquid crystal compounds known to date are few.

Whether the liquid crystal compound has an antiferroelectric phase or not greatly depends on the structure of the liquid crystal compound and presence or absence of the substituent. Compounds involved in Japanese Laid-open Patent Appln. (Kokai) No. 316372/1989 are taken as an example. The belowdescribed compound (A) has a ferroelectric phase ($S_C*$) and an antiferroelectric phase ($S_{CA}*$), while the belowdescribed compound (B) has only a ferroelectric phase but not an antiferroelectric phase. Thus, even if the compounds are identical in e.g. core structure, the presence or absence of the antiferroelectric phase of the liquid crystal compounds is determined by a slight difference in number of carbon atoms, presence or absence of the substituent, etc. It can be understood that since both the compounds (A) and (B) have the ferroelectric phase ($S_C*$), the antiferroelectric phase depends more on the structure of the liquid crystal compound than the ferroelectric phase ($S_C*$).

Compound-A

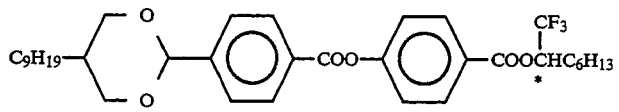

crystal $\xrightleftharpoons[18.0° C.]{52.5° C.}$ $S_{CA}*$ $\xrightleftharpoons{70.0° C.}$ $S_C*$ $\xrightleftharpoons{71.5° C.}$ $S_A$ $\xrightleftharpoons{79.9° C.}$ isotropic phase Compound-B

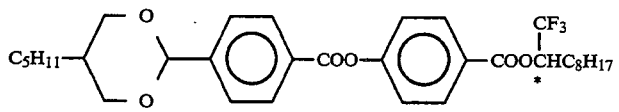

crystal $\xrightleftharpoons[-28.5° C.]{-28° C.}$ $S_C*$ $\xrightleftharpoons{98° C.}$ isotropic phase On the other hand, Japanese Laid-open Patent Appln. (Kokai) No. 213390/1989 describes a ferroelectric chiral smectic Y (this is considered an anti ferro electric liquid crystal phase) liquid crystal composition comprising at least two of 43 concrete compounds. The 43 compounds have the following basic chemical structure.

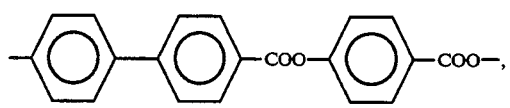

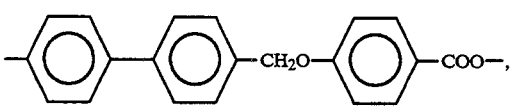

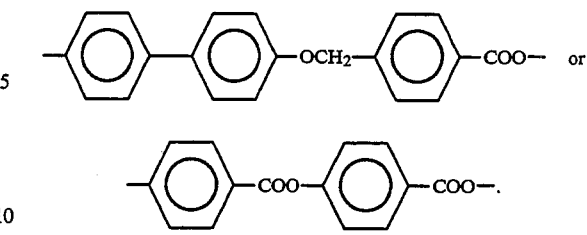

Alkyl groups or alkoxy groups on the right or left side are specified to have a combination of special structures and a type and a position of a halogen as a substituent in benzene ring are specified. It is thus understood that the compound used as a ferroelectric chiral smectic Y liquid crystal composition is limited to a compound having a specific combination of a structure and a substituent. According to the present inventors' research works, it is ascertained that when the compound having the structure of

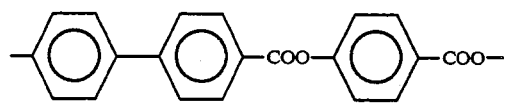

has fluorine in the benzene ring, a response speed is low.

As is apparent from the foregoing, it is now impossible to infer from the chemical structure whether the liquid crystal compounds have an antiferroelectric phase or not. Whether the liquid crystal compounds have an antiferroelectric phase or not is clarified by measuring the physical properties of said compounds.

It is an object of this invention to provide a novel liquid crystal compound having the antiferroelectric phase.

Another object of this invention is to provide a liquid crystal compound which has tristable switching characteristics, sharp thresholds and good memory effect and which can be used as a liquid crystal display device.

Still another object of this invention is to provide a liquid crystal compound that can be used in a high-performance, large-sized liquid crystal display having high-speed response.

Yet another object of this invention is to provide a liquid crystal compound that can be used in a high-performance, large-sized liquid crystal display.

A further object of this invention is to provide a liquid crystal device that can be produced at a relatively low cost, industrially.

The other objects of this invention will be made clear from the following description.

MEANS FOR SOLVING THE PROBLEMS

According to the present inventors' studies, it is found that the objects and advantages of this invention can be achieved by a liquid crystal compound represented by formula (I)

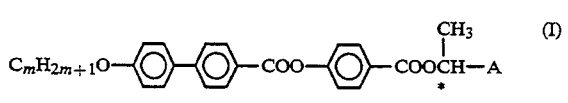

wherein A represents —$C_3H_7$, —$C_4H_9$ or —$C_8H_{17}$; when A is —$C_3H_7$, m is an integer of 8, 10, 12 or 14; and when A is —$C_4H_9$ or —$C_8H_{17}$, m is an integer of 7 to 14, said compound having an antiferroelectric phase.

This invention will be described in more detail below.

In the compound of formula (I) in this invention, $C_mH_{2m+1}$— is an alkyl group having a number of carbon atoms depending on the group A, and this alkyl group is a linear alkyl group (i.e. a normal alkyl group). —$C_3H_7$, —$C_4H_9$ and —$C_8H_{17}$ represented by A are also linear alkyl groups (i.e. normal alkyl groups).

The compound of formula (I) in this invention can be divided into the following three groups based on the type of the group A.

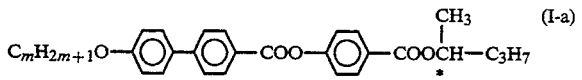

wherein m is an integer of 8, 10, 12 or 14.

The compound of formula (I-a) wherein m is 7 or less, 9, 11, 13, or 15 or more has no antiferroelectric phase.

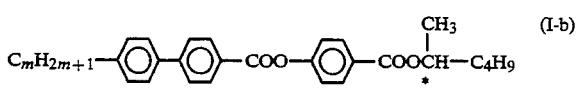

wherein m is an integer of 7 to 14.

The compound of formula (I-b) wherein m is 6 or less, or 15 or more has no antiferroelectric phase.

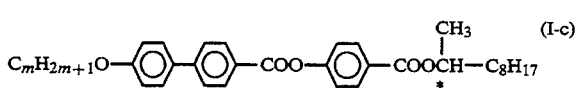

wherein m is an integer of 7 to 14.

The compound of formula (I-c) wherein m is 6 or less, or 15 or more has no antiferroelectric phase.

In the compound of formula (I) in this invention, the carbon atom marked with * is an asymmetric carbon atom. The compound of formula (I) in this invention can be synthesized by any method. A reaction scheme is shown below.

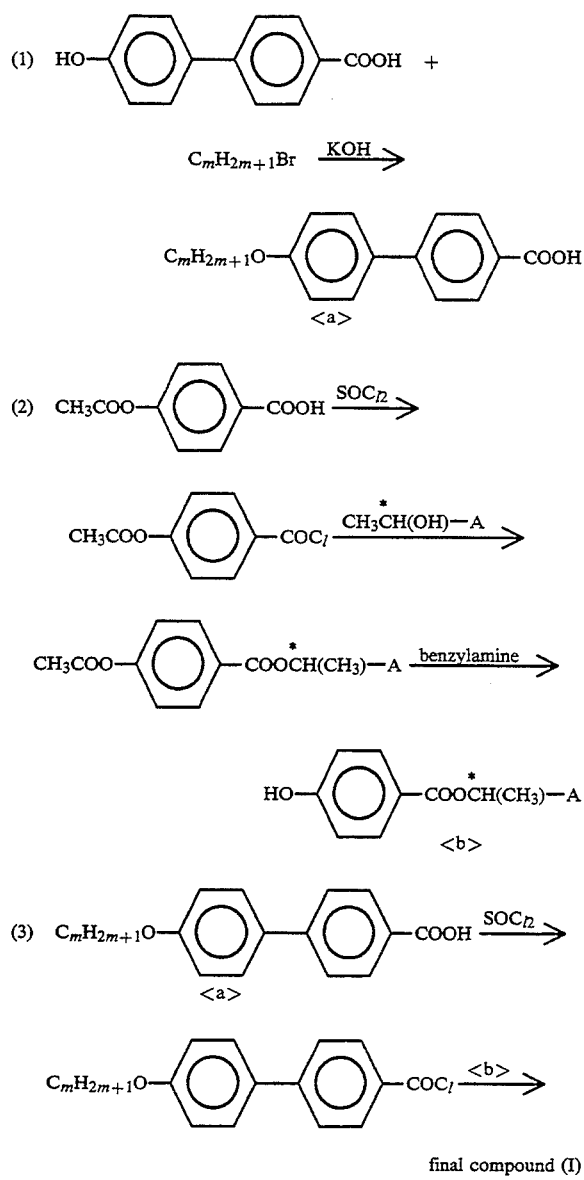

final compound (I)

In the above reaction scheme, A and m are as defined in formula (I).

In the compound of formula (I) in this invention, a compound wherein when A is —$C_3H_7$, m is 8, is preferable. A compound wherein when A is —$C_4H_9$ or —$C_8H_{17}$, m is 7 to 10, especially 8 or 9, is especially preferable. Above all, the compounds of the following 5 formulas (1) to (4) are excellent because a response speed is high and sharp thresholds are shown.

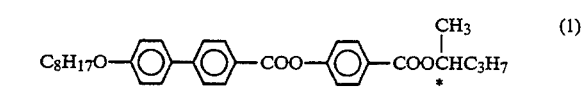

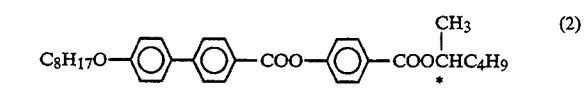

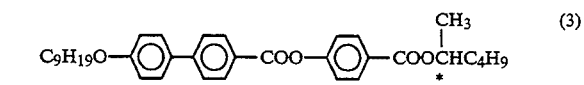

-continued

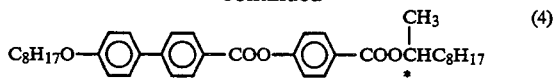

One or more of the liquid crystal compounds represented by formula (I) in this invention are mixed with the other liquid crystal compounds and used in the aforesaid various fields as liquid crystal display devices.

EFFECTS OF THE INVENTION

This invention can provide a novel liquid crystal compound having an antiferroelectric phase. The novel liquid crystal compound provided by this invention can be used as a liquid crystal display device having tristable switching, sharp threshold characteristic, good memory effect and an excellent response speed.

EXAMPLES

Figure 1:
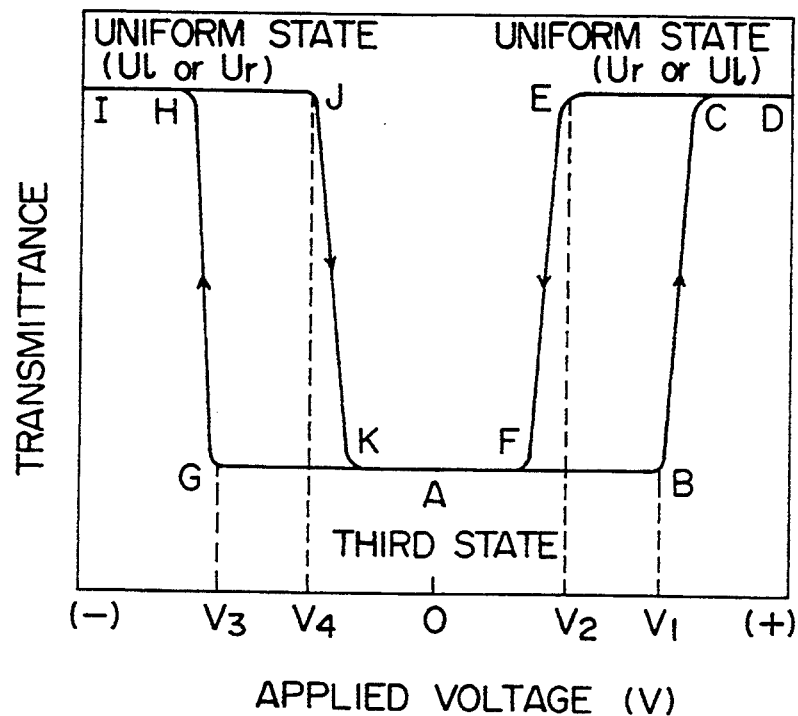
FIG. 1 is a view showing an optical response hysteresis in a usual antiferroelectric phase.

The following Examples and Comparative Examples illustrate this invention more specifically. This invention is however not limited thereto.

Example 1

1) Preparation of 4-(4'-n-octyloxy)biphenylcarboxylic Acid (1)

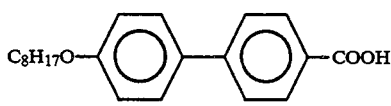

4-(4'-Hydroxy)biphenylcarboxylic acid (10.5 g), 14.0 g of n-octyl bromide and 6.45 g of potassium hydroxide were added to a mixed solution of 1500 ml of ethanol and 200 ml of water, and the reaction was run under reflux for 10 hours. Further, 500 ml of water was added, and the mixture was stirred for 3 hours. After the reaction, the resulting mixture was acidified with conc. hydrochloric acid. The solvent (500 ml) was evaporated, and the reaction product was cooled to room temperature to obtain a white solid. The white solid was thoroughly washed with water and recrystallized from chloroform to afford 12.5 g of a final compound as a white crystal.

2) Preparation of 4-acetoxy-1-(1-methylbutyloxycarbonyl)benzene (2)

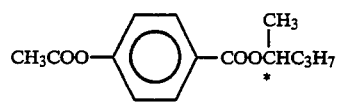

4-Acetoxybenzoic acid (6.2 g) was added to 25 ml of thionyl chloride, and the reaction was conducted under reflux for 10 hours. After excess thionyl chloride was distilled off, 15 ml of pyridine and 90 ml of toluene were added. Two grams of optically active S-(+)-2-pentanol was added dropwise thereto. After the addition, the mixture was heated under reflux for 4 hours, left to cool and diluted with 500 ml of chloroform. The organic layer was washed with dilute hydrochloric acid, a 1N sodium hydroxide aqueous solution and water in this order, and dried with magnesium sulfate. Further, the solvent was evaporated to obtain 2.2 g of a final crude compound.

3) Preparation of 4-hydroxy-1-(1-methylbutyloxycarbonyl)benzene (3)

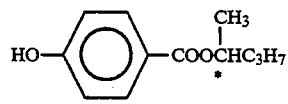

Two grams of the crude compound (2) was dissolved in 50 ml of ethanol and 4 g of benzylamine was added dropwise. The mixture was stirred at room temperature for 4 hours, then diluted with 500 ml of chloroform, washed with dilute hydrochloric acid and water in this order, and dried with magnesium sulfate. After the solvent was evaporated, the residue was subjected to isolation and purification by silica gel column chromatography to obtain 1.6 g of a final compound.

4) Preparation of 4-(1-methylbutyloxycarbonylphenyl)-4'-n-octyloxybiphenyl-4-carboxylate (4)

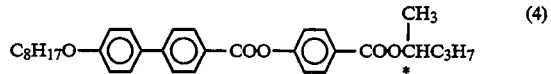

Figure 4:
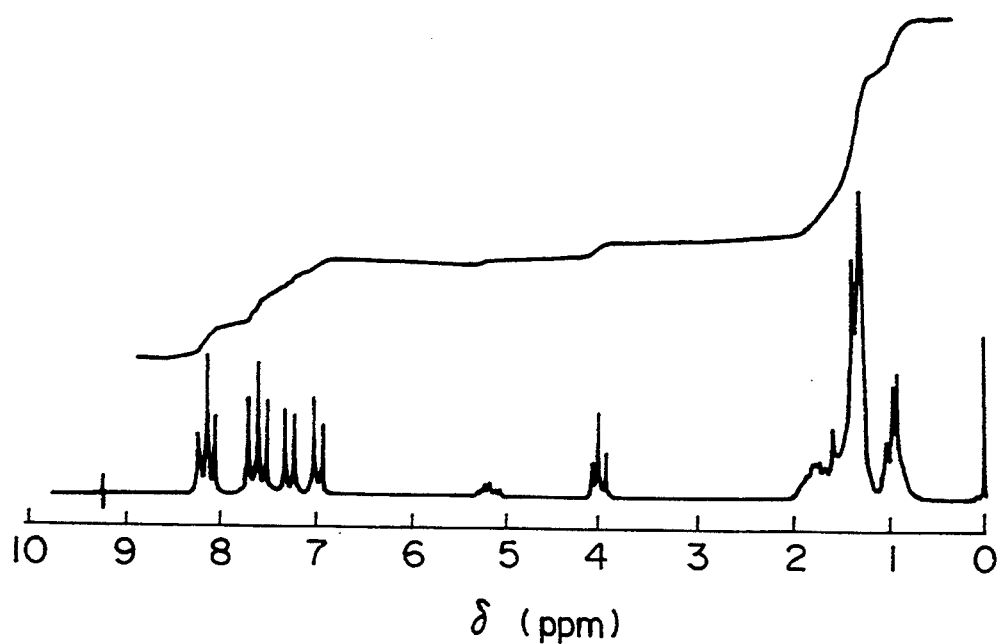
FIGS. 4, 5, 6 and 7 show nuclear magnetic resonance spectra ('H-NMR) of liquid crystal compounds (4), (6), (8) and (12) in this invention which will be later described in Examples.

To 1.2 g of the above compound (1) was added 10 ml of thionyl chloride, and the mixture was heated under reflux for 10 hours. After excess thionyl chloride was evaporated, 20 ml of pyridine and 60 ml of toluene were added, and 20 ml of a toluene solution containing 0.5 g of the compound (3) was added dropwise. The reaction was run at room temperature for 10 hours. After the reaction, the reaction mixture was diluted with 500 ml of chloroform, and washed with dilute hydrochloric acid, a 1N sodium hydroxide aqueous solution and water in this order. The organic layer was dried with magnesium sulfate. After the solvent was evaporated, the residue was subjected to isolation by silica gel column chromatography. The resulting product was then recrystallized from ethanol to obtain 0.8 g of a final compound (4). A nuclear magnetic resonance spectrum ('H-NMR) of the final compound is shown in FIG. 4. Identification of liquid crystal phases was carried out by observation of a texture and measurement of DSC (differential scanning calorimeter).

Figure 5:
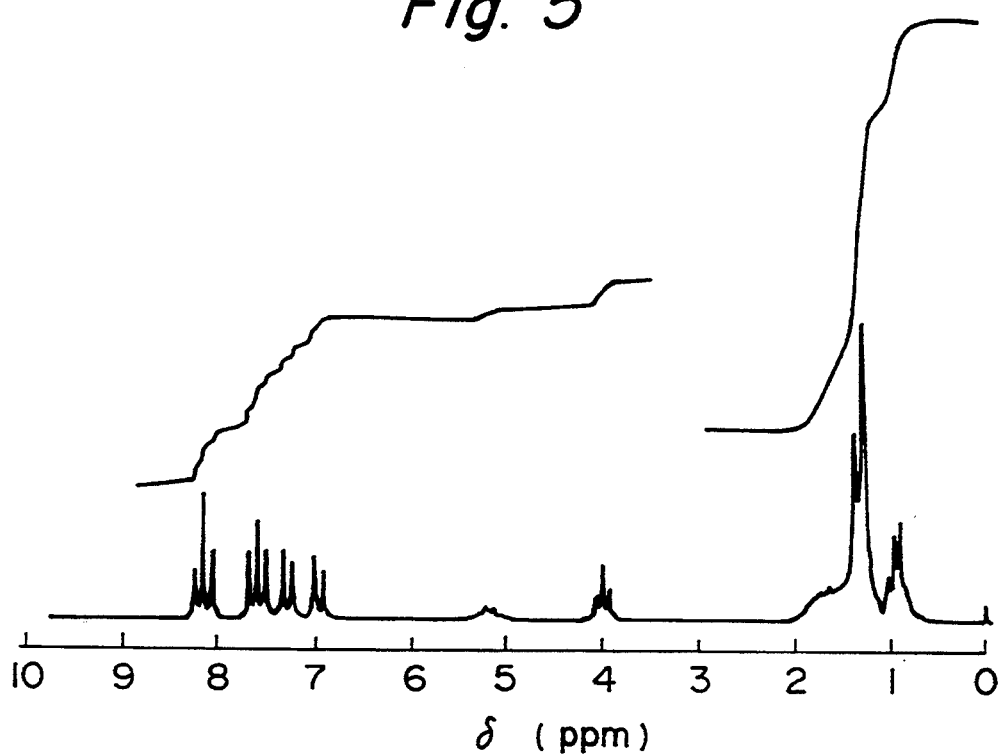

Phase transition temperatures of the compound (4) in Example 1 are as follows.

a final compound (6). A nuclear magnetic resonance spectrum ('H-NMR) of the final compound is shown in FIG. 5. Identification of liquid crystal phases was carried out by observation of a texture and measurement by DSC.

Phase transition temperatures of the compound (6) in Example 2 are shown as follows.

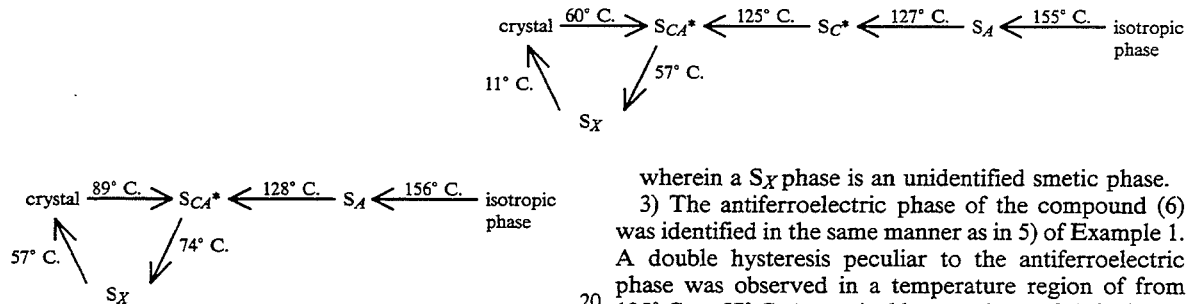

wherein a $S_X$ phase is an unidentified smetic phase.

Figure 2:
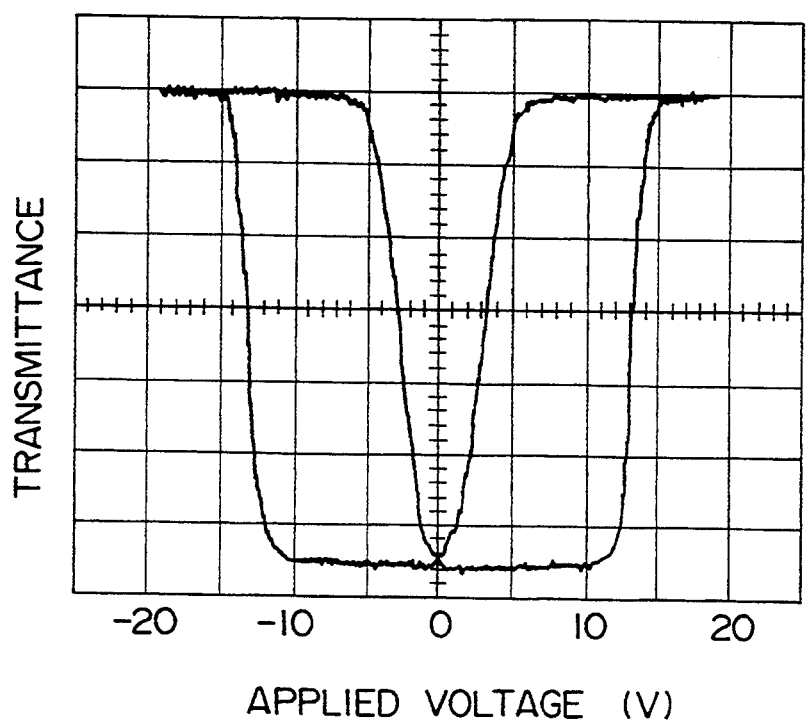
FIGS. 2 and 3 show optical response hysteresis of liquid crystal compounds (6) and (8) in this invention which will be later described in Examples.

3) The antiferroelectric phase of the compound (6) was identified in the same manner as in 5) of Example 1. A double hysteresis peculiar to the antiferroelectric phase was observed in a temperature region of from 125° C. to 57° C. An optical hysteresis at 80° C. is shown in FIG. 2.

Example 3

1) Preparation of 4-(4'-n-dodecanoxy)biphenylcarboxylic acid (7)

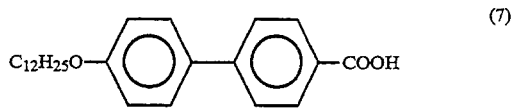

The procedure in 1) of Example 1 was repeated except that 14.0 g of n-octyl bromide was replaced with 18.2 g of n-dodecyl bromide. There resulted 14.6 g of a final compound (7).

2) Preparation of 4-( 1-methylbutyloxycarbonylphenyl)-4'-n-dodecanoxybiphenyl- 4-carboxylate (8)

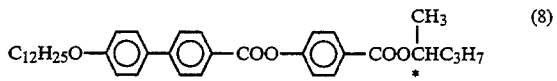

Figure 6:
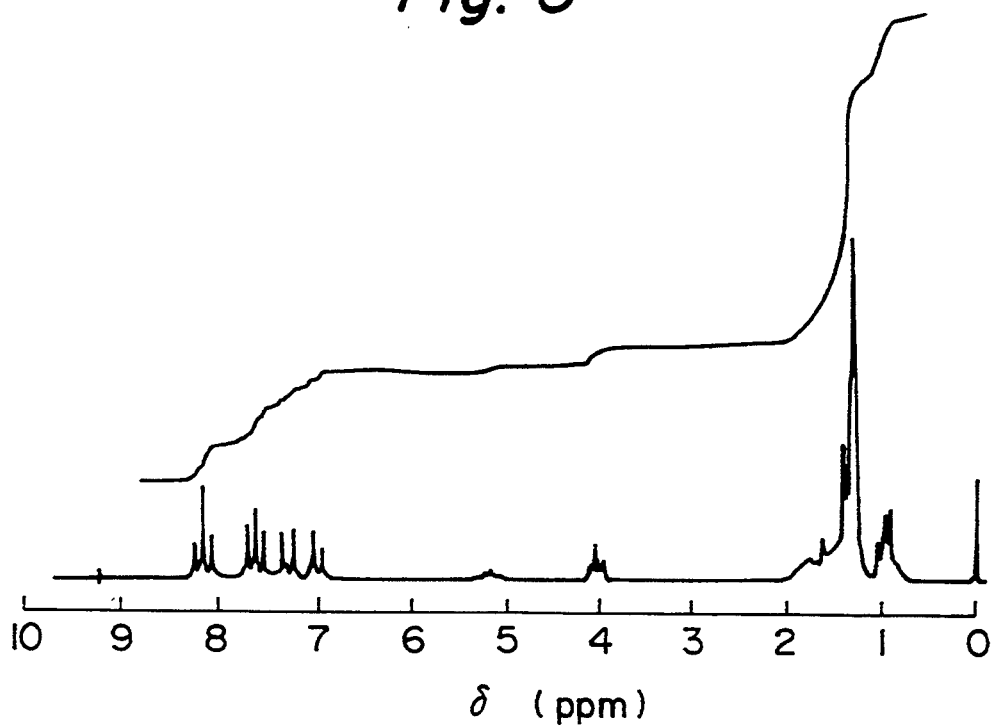

The procedure in 4) of Example 1 was repeated except that 1.2 g of the compound (1) in Example 1 was replaced with 1.4 g of the compound (7). There was obtained 0.7 g of a final compound (8). A nuclear magnetic resonance spectrum ('H-NMR) of the final compound (8) is shown in FIG. 6. Identification of phases was carried out by observation of a texture and measurement by DSC.

Phase transition temperatures of the compound (8) in Example 3 are as follows.

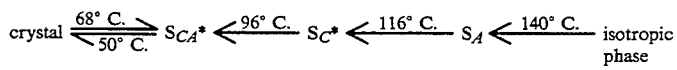

Figure 3:
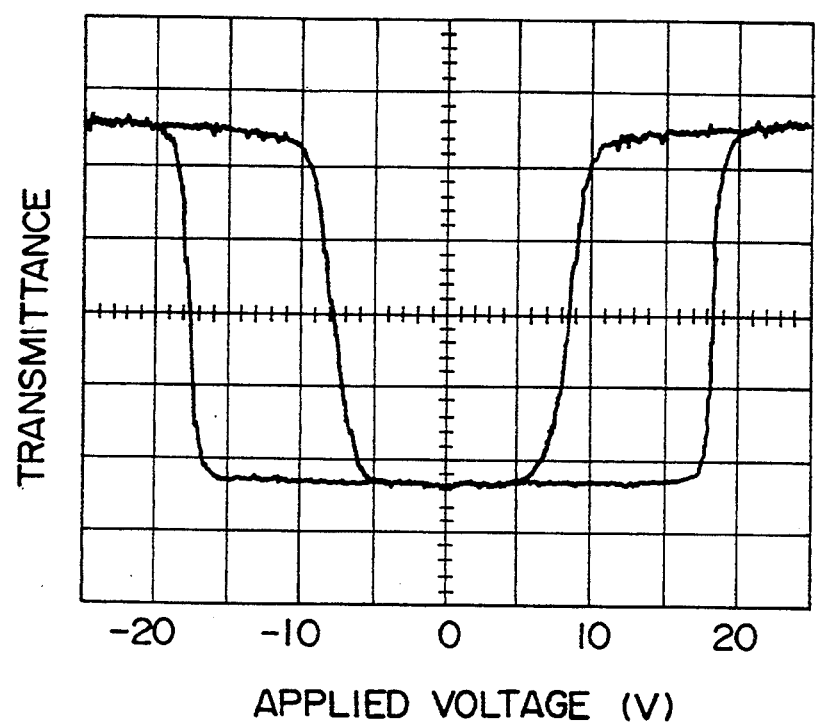

3) The antiferroelectric phase of the compound (8) was identified in the same way as in 5) of Example 1. As a result, a double hysteresis peculiar to the antiferroelectric phase was observed in a temperature region of from 96° C. An optical response hysteresis at 90° C. is shown in FIG. 3.

wherein a $S_X$ phase is an unidentified smectic phase.

5) The antiferroelectric phase was identified in the following manner.

A liquid crystal cell (a cell thickness 3 micrometers) with an ITO electrode having a rubbed polyimide thin film was filled with the compound (4) in an isotropic phase. The cell was slowly cooled at a rate of 1.0° C. per minute, and the liquid crystal was aligned in a $S_A$ phase. The cell was disposed between intersecting deflection plates such that the layer direction of the liquid crystal was parallel to an analyzer or a polarizer. A triangular wave voltage of ±40 V and 0.2 Hz was applied to the cell and the transmittance was measured by a photomultiplier. As a result, a double hysteresis peculiar to the antiferroelectric phase was observed in a temperature region of from 128° C. to 74° C.

Example 2

1) Preparation of 4-(4'-n-decanoxy)biphenylcarboxylic acid (5)

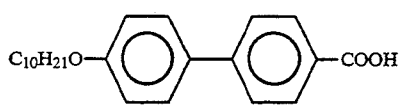

The procedure on 1) of Example 1 was repeated except that 14.0 g of n-octyl bromide was replaced with 16.2 g of n-decyl bromide. There resulted 9.2 g of the final compound (5).

2) Preparation of 4-(1-methylbutyloxycarbonylphenyl)-4'-n-decanoxybiphenyl-4-carboxylate (6)

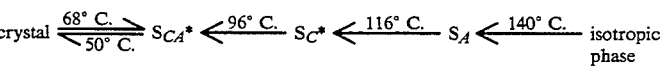

The procedure in 4) of Example 1 was repeated except that 1.2 g of the compound (1) was replaced with 1.3 g of the compound (5). There was obtained 0.6 g of

Example 4

1) Preparation of 4-(4'-n-tetradecanoxy)-biphenylcarboxylic acid (11)

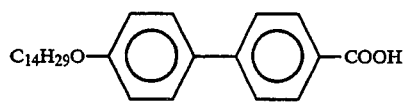
(11)

The procedure in 1) of Example 1 was followed except 14.0 g of n-octyl bromide was replaced with 20.3 g of n-tetradecanol bromide. There was obtained 15.1 g of a final compound (11).

2) Preparation of 4-(1-methylbutyloxycarbonylphenyl)-4'-n-tetradeconoxybiphenyl-4-carboxylate (12)

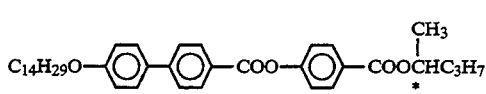
(12)

Figure 7:
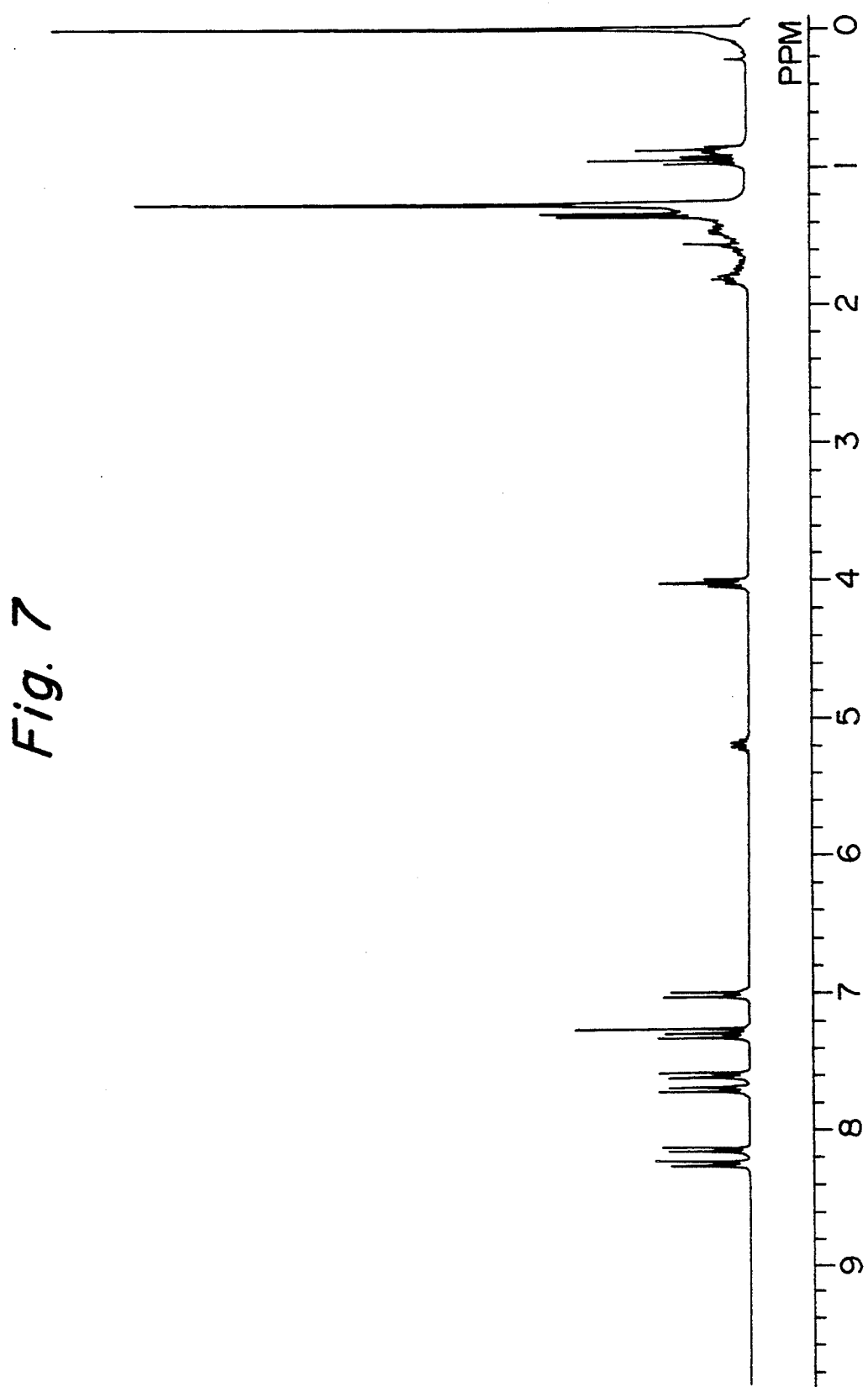

The procedure in 4) of Example 1 was replaced with 1.4 g of the compound (11). There was obtained 0.7 g of a final compound (12). A nuclear magnetic resonance spectrum (H'-NMR) of the final compound (12) is shown in FIG. 7. Identification of phases was conducted by observation of a texture and measurement by DSC.

Phase transition temperatures of the compound (12) in Example 4 are as follows.

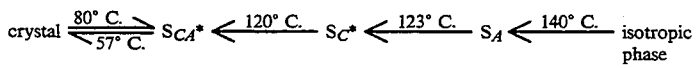

Comparative Example 1

1) Preparation of 4-(4'-n-heptyloxy) biphenylcarboxylic acid (13)

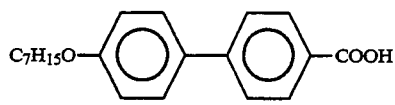
(13)

The procedure in 1) of Example 1 was followed except that 14.0 g of n-octyl bromide was replaced with 13.2 g of n-heptyl bromide, There was obtained 11.1 g of a final compound ( 13 ).

2) Preparation of 4-(1-methylbutyloxycarbonylphenyl)-4'-n-heptyloxybiphenyl-4-carboxylate (14)

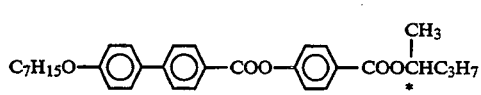
(14)

The procedure in 4) of Example 1 was followed except that 1.2 g of the compound (1) was replaced with 1.1 g of the compound (13), There was obtained 0.5 g of a final compound (14).

Phase transition temperatures of the compound (14) are as follows, There was no antiferroelectric phase.

Comparative Example 2

1) Preparation of 4-(4'-n-nonyloxy) biphenylcarboxylic acid (15)

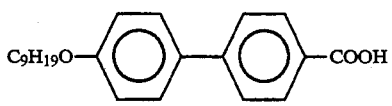
(15)

The procedure in 1) of Example 1 was followed except that 14.0 g of n-octyl bromide was replaced with 15.2 g of n-nonyl bromide. There resulted 12.6 g of a final compound (15).

2) Preparation of 4-(1-methylbutyloxycarbonylphenyl)-4'-n-nonyloxybiphenyl-4-carboxylate (16)

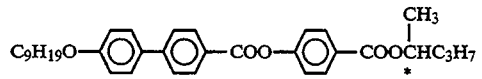
(16)

The procedure in 4) of Example 1 was followed except that 1.2 g of the compound (1) was replaced with 1.35 g of the compound (15). There was obtained 0.7 g of a final compound (16).

Phase transition temperatures of the compound (16) are as follows. There was no antiferroelectric phase.

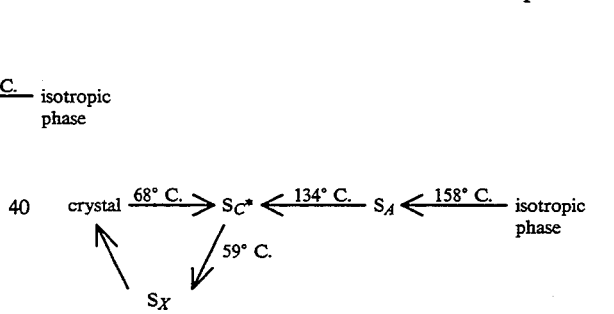

Comparative Example 3

1) Preparation of 4-(4'-n-dodecanoxy)biphenylcarboxylic acid (17)

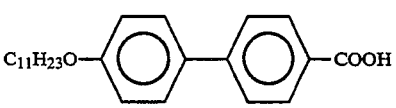
(17)

The procedure in 1) of Example 1 was followed except that 14.0 g of n-octyl bromide was replaced with 17.3 g of n-dodecyl bromide. There was obtained 14.5 g of a final compound (17).

2) Preparation of 4-(1-methylbutyloxycarbonylphenyl)-4'-n-dodecanoxybiphenyl-4-carboxylate (18)

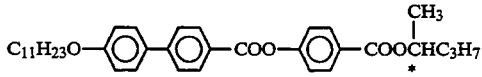
(18)

The procedure in 4) of Example 1 was followed except that 1.2 g of the compound (1) in Example 1 was replaced with 1.4 g of the compound (17). There was obtained 0.4 g of a final compound (18).

Phase transition temperatures of the compound (18) are as follows. There was no antiferroelectric phase.

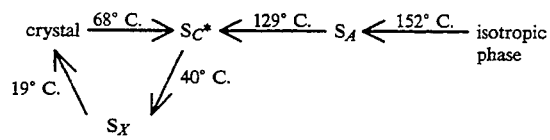

wherein a $S_X$ phase is an unidentified smectic phase.

Example 5

1) Preparation of 4-(4′-n-heptyloxy)biphenylcarboxylic acid (a)

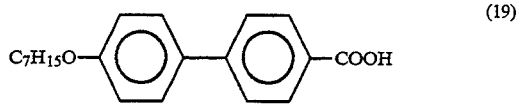

The procedure in 1) of Example 1 was followed except that 14.0 g of n-octyl bromide was replaced with 13.0 g of n-heptyl bromide. There was obtained 12.5 g of a final compound (19).

2) Preparation of 4-acetoxy-1-(1-methylpentyloxycarbonyl)benzene (20)

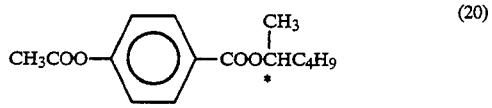

4-Acetoxybenzoic acid (6.2 g) was added to 15 ml of thionyl chloride, and the reaction was run under reflux for 10 hours. After excess thionyl chloride was evaporated, 15 ml of pyridine and 90 ml of toluene were added and 2.0 g of optically active S-(+)-2-hexanol was added dropwise. After the addition, the mixture was heated under reflux for 4 hours, left to cool, and diluted with 500 ml of chloroform. The organic layer was washed with dilute hydrochloric acid, a 1N sodium hydroxide aqueous solution and water in this order, and dried with magnesium sulfate. Further, the solvent was evaporated to obtain 2.2 g of a final crude compound (20).

3) Preparation of 4-hydroxy-1-(1-methylpentyloxycarbonyl)benzene (21)

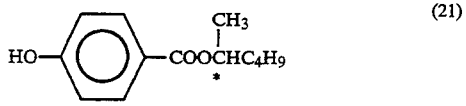

Two grams of the crude product (20) was dissolved in 50 ml of ethanol, and 4 g of benzylamine was added dropwise thereto. The mixture was stirred at room temperature for 4 hours, diluted with 500 ml of chloroform, washed with dilute hydrochloric acid and water in this order and dried with magnesium sulfate. After the solvent was evaporated, the residue was subjected to isolation and purification by silica gel column chromatography. There was obtained 1.6 g of a final compound (21).

4) Preparation of 4-(1-methylpentyloxycarbonylphenyl)-4′-n-heptyloxybiphenyl-4-carboxylate (22)

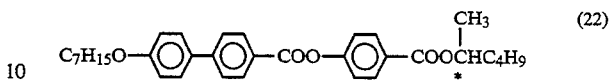

Figure 11:
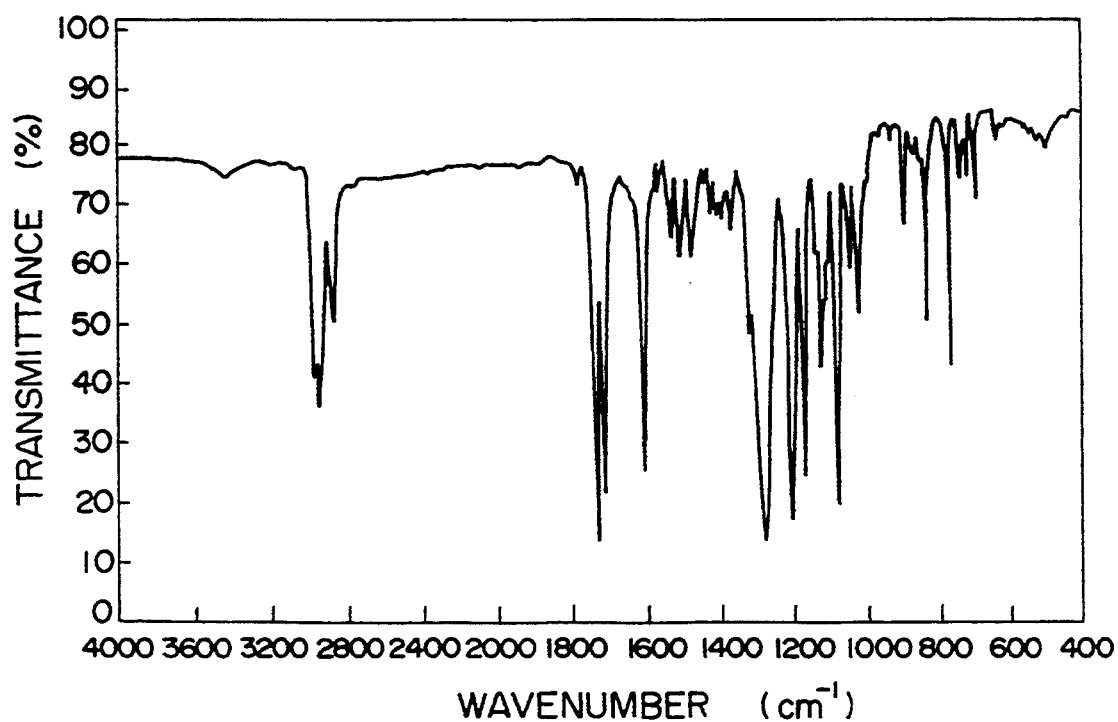
FIGS. 11, 12, 13 and 14 show infrared absorption spectra of liquid crystal compounds (22), (24), (26) and (28) in this invention which will be later described in Examples.

To 1.2 g of the compound (19) was added 10 ml of thionyl chloride, and the mixture was heated under reflux for 10 hours. After excess thionyl chloride was evaporated, 10 ml of pyridine and 60 ml of toluene were added, and 20 ml of a toluene solution containing 0.5 g of the compound (21) was then added dropwise, followed by the reaction at room temperature for 10 hours. After the reaction, the reaction mixture was diluted with 500 ml of chloroform and washed with dilute hydrochloric acid, a 1 N sodium hydroxide aqueous solution and water in this order. The organic layer was dried with magnesium sulfate. After the solvent was evaporated, the residue was subjected to isolation and purification by silica gel column chromatography. The resulting product was recrystallized from ethanol to obtain 0.8 g of a final compound (22). An infrared absorption spectrum (KBr) of the final compound is shown in FIG. 11. Identification of phases was carried out by observation of a texture and measurement by DSC.

Phase transition temperatures of the compound (22) in Example 5 are as follows.

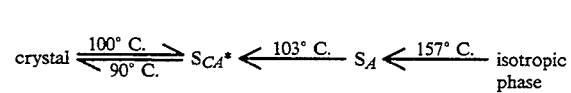

Figure 8:
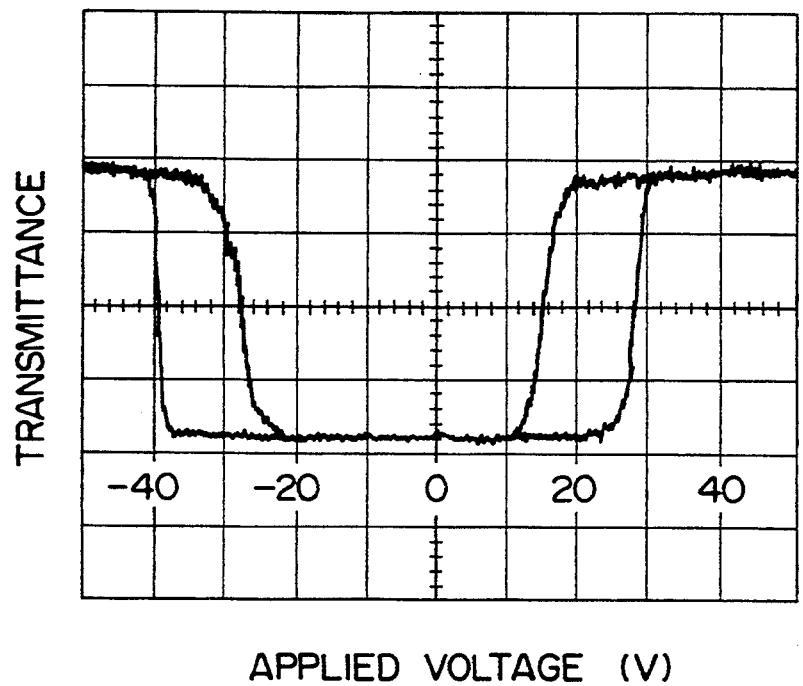
FIGS. 8, 9 and 10 show optical response hysteresis of liquid crystal compounds (22), (24) and (26) in this invention which will be later described in Examples.

5) The antiferroelectric phase of the compound (22) was identified in the same way as in 5) of Example 1. Consequently, a double hysteresis peculiar to the antiferroelectric phase was observed in a temperature region of from 108° C. to 90° C. An optical response hysteresis at 92° C. is shown in FIG. 8.

Example 6

1) Preparation of 4-(4′-n-octyloxy)biphenylcarboxylic acid (23)

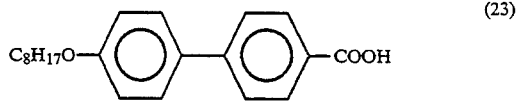

The procedure in 1) of Example 5 was followed except that 13.0 g of n-heptyl bromide was replaced with 14.0 g of n-octyl bromide. There was obtained 12.5 g of a final compound (23).

2) Preparation of 4-(1-methylpentyloxycarbonylphenyl)-4′-n-octyloxybiphenyl-4-carboxylate (24)

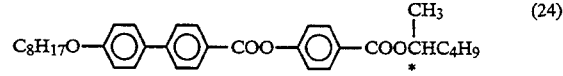

Figure 12:
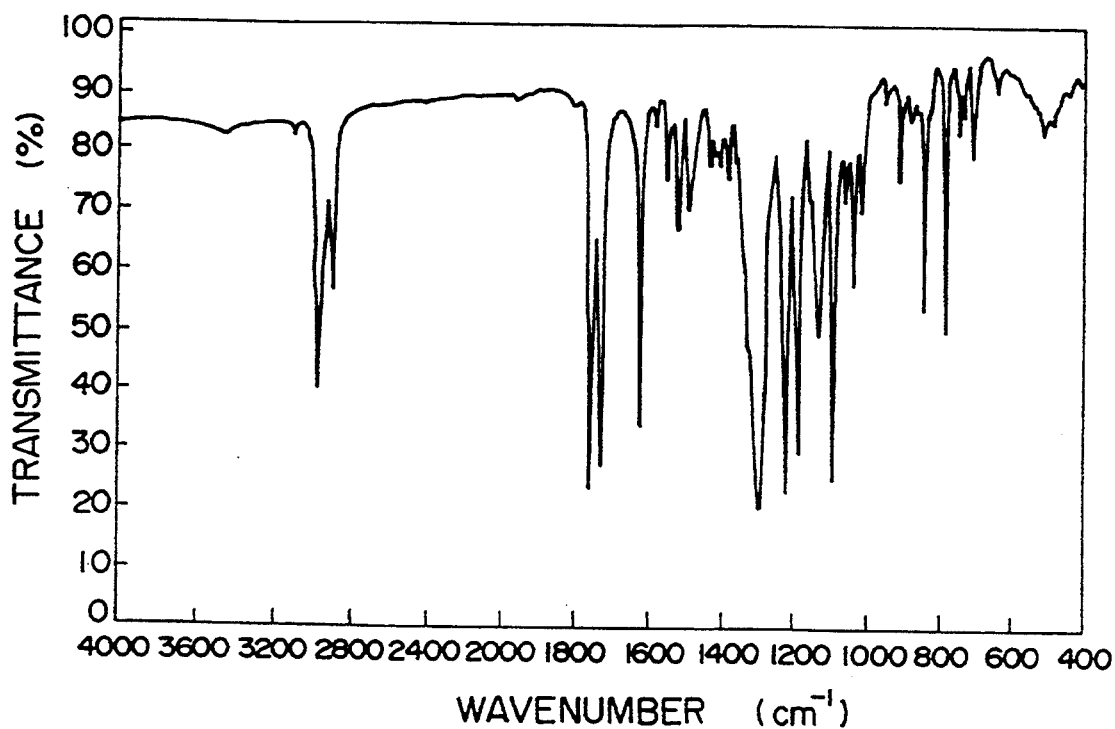

The procedure in 4) of Example 5 was followed except that 1.2 g of the compound (19) in Example 5 was replaced with 1.3 g of the compound (23). There resulted 1.1 g of a final compound (24). An infrared absorption spectrum (KBr) of the final compound is shown in FIG. 12. Identification of phases was carried out by observation of a texture and measurement by DSC.

Phase transition temperatures of the compound (24) in Example 6 are as follows.

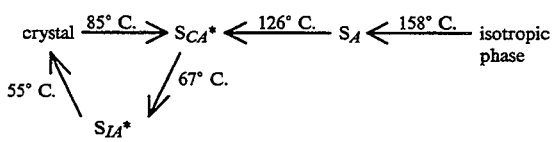

Figure 9:
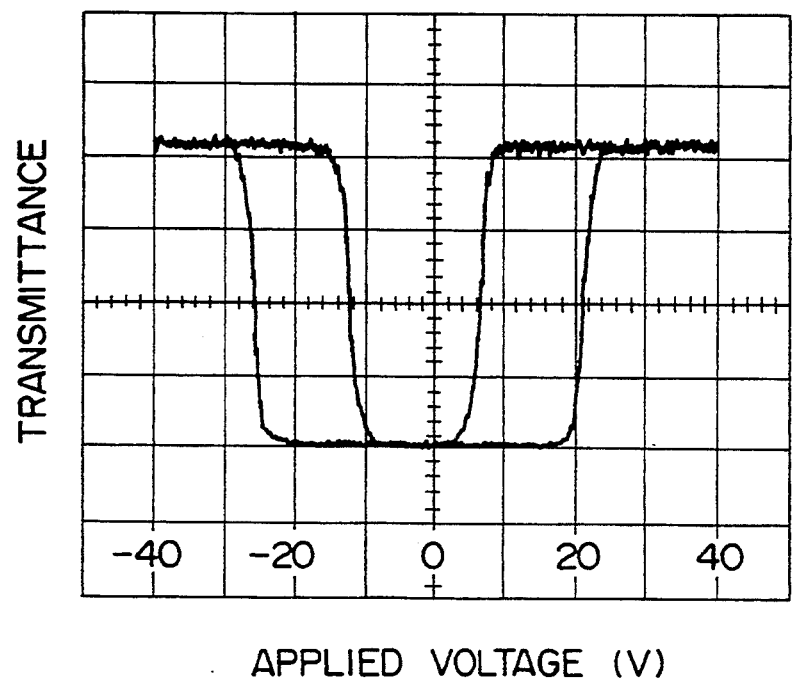

3) The antiferroelectric phase of the compound (24) was identified in the same way as in 5) of Example 1. A double hysteresis peculiar to the antiferroelectric phase was observed in a temperature region of from 126° C. to 55° C. An optical response hysteresis at 90° C. is shown in FIG. 9.

Example 7

1) Preparation of 4-(4'-n-dodecanoxy)biphenylcarboxylic acid (25)

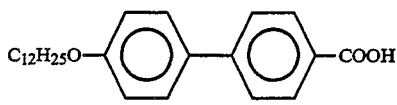

The procedure in 1) of Example 5 was followed except that 13.0 g of n-heptyl bromide was replaced with 18.1 g Of n-dodecyl bromide. There was obtained 9.2 g of a final compound (25).

2) Preparation of 4-(1-methylpentyloxycarbonylphenyl)-4'-n-dodecanoxybiphenyl-4-carboxylate (26)

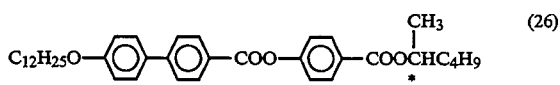

Figure 13:
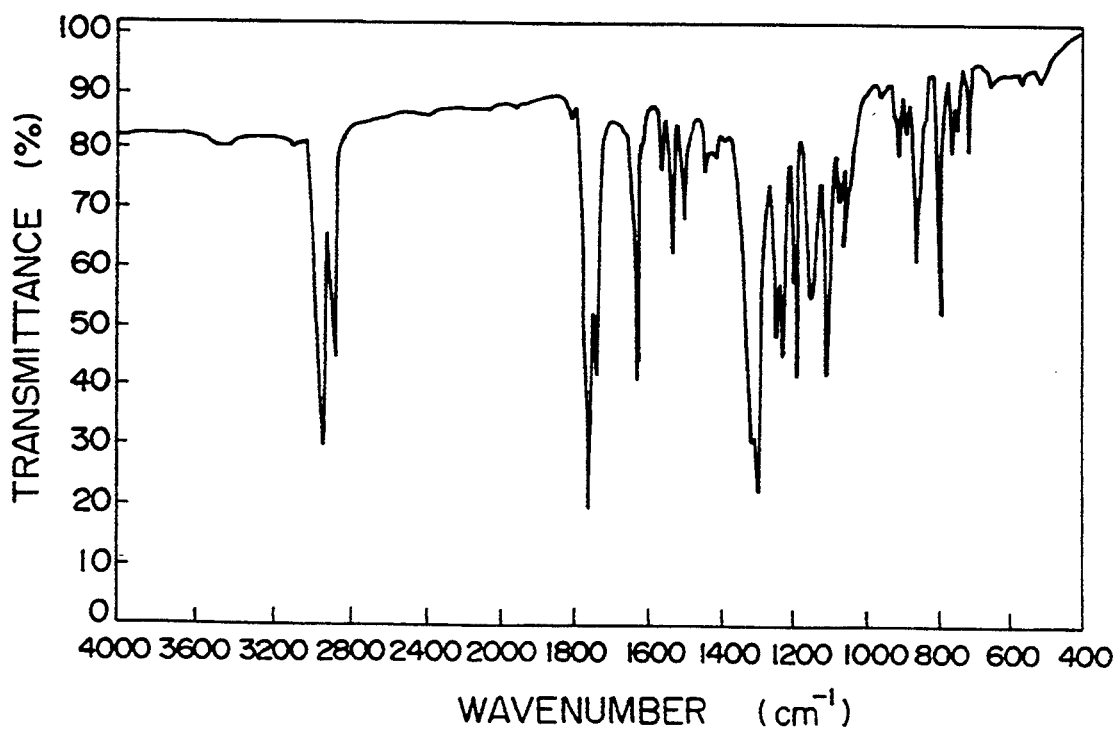

The procedure in 4) of Example 5 was followed except that 1.2 g of the compound (19) in Example 5 was replaced with 1.3 g of the compound (25). There was obtained 0.9 g of a final compound (26). An infrared absorption spectrum (KBr) of the final compound is shown in FIG. 13. Identification of phases was carried out by observation of a texture and measurement by DSC.

Phase transition temperatures of the compound (26) in Example 7 are as follows.

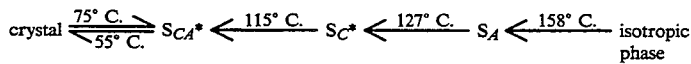

Figure 10:
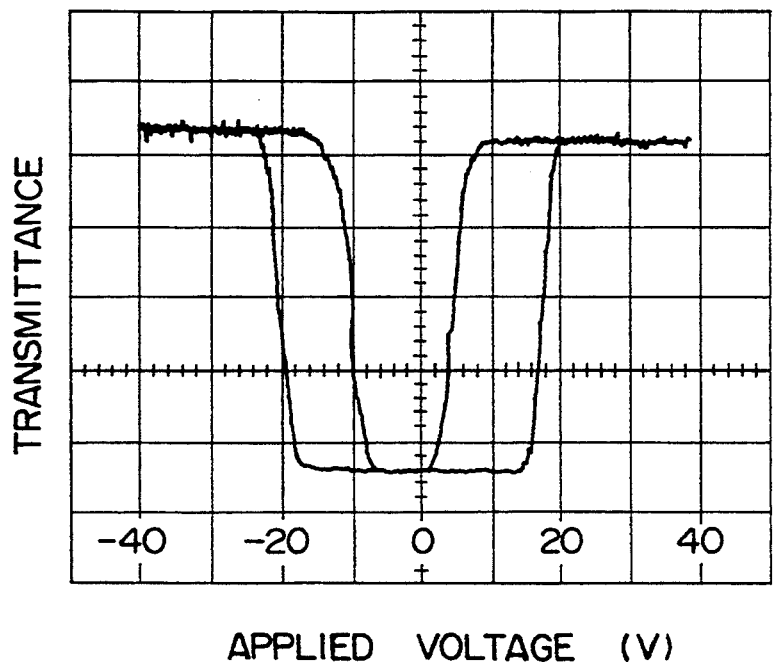

3) The antiferroelectric phase of the compound (26) was identified in the same way as in 5) of Example 1. As a result, a double hysteresis peculiar to the antiferroelectric phase was observed in a temperature region of from 115° C. to 55° C. An optical response hysteresis at 90° C. is shown in FIG. 10.

Example 8

1) Preparation of 4-(4'-n-tetradecanoxy)-biphenylcarboxylic acid (27)

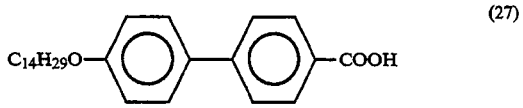

The procedure in 1) of Example 5 was followed except that 13.0 g of n-heptyl bromide was replaced with 20.1 g of n-tetradecanyl bromide. There resulted 18.5 g of a final compound (27).

2) Preparation of 4-(1-methylpentyloxycarbonylphenyl)-4'-n-tetradecanoxybiphenyl-4-carboxylate (28)

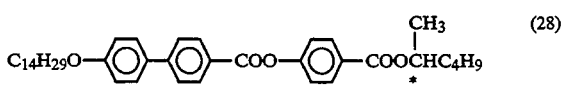

Figure 14:
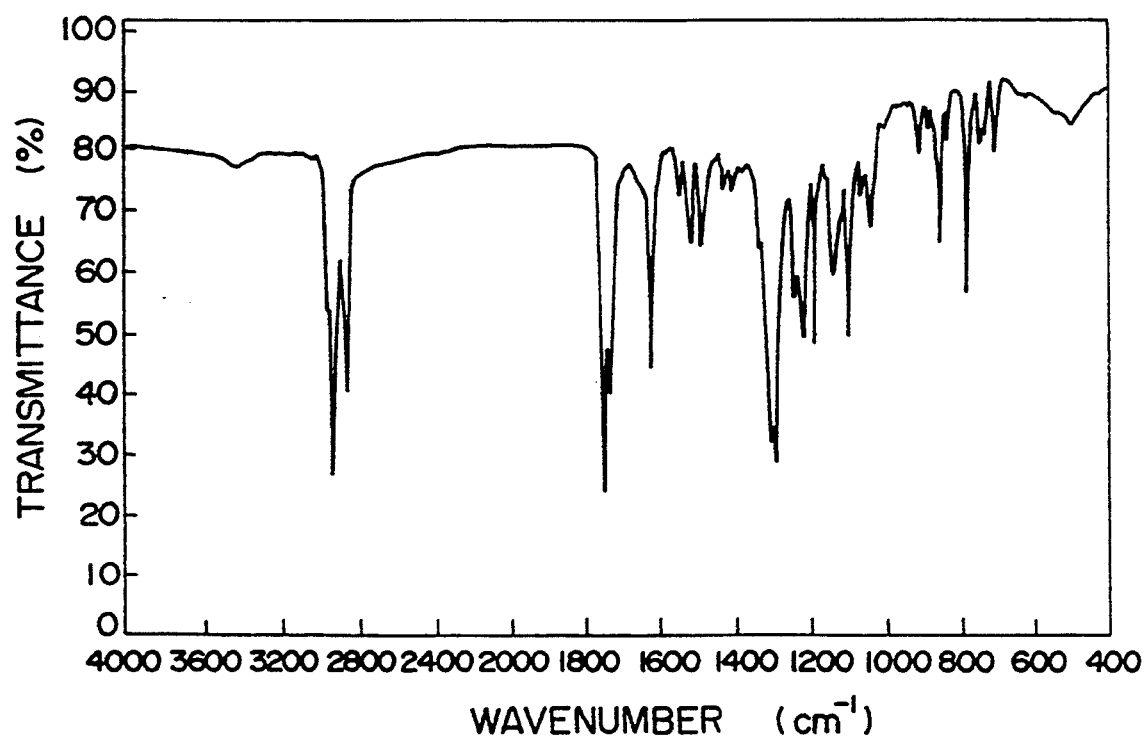

The procedure in 4) of Example 5 was followed except that 1.2 g of the compound (19) in Example 5 was replaced with 1.3 g of the compound (27). There resulted 0.9 g of the final compound (28). An infrared absorption spectrum (KBr) of the final compound (28) is shown in FIG. 14. Identification of phases was carried out by observation of a texture and measurement by DSC.

Phase transition temperatures of the compound (28) in Example 8 are as follows.

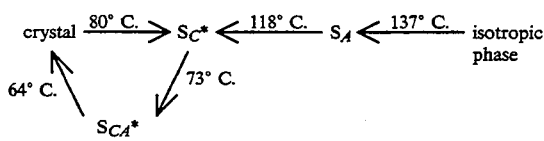

The antiferroelectric phase of the compound (28) was in a supercooled state and unstable thermodynamically so that an optical response could not be observed. However, since an extinction direction was along the layer normal to the phase and a threshold was present, the antiferroelectric phase existed undoubtedly.

Comparative Example 4

1) Preparation of 4-(4'-n-hexyloxy)biphenylcarboxylic acid (29)

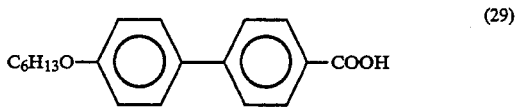

The procedure in 1) of Example 5 was followed except that 13.0 g of n-heptyl bromide was replaced with 12.0 g of n-hexyl bromide. There resulted 8.2 g of a final compound (29).

2) Preparation of 4-(1-methylpentyloxycarbonylphenyl)-4′-n-hexyloxybiphenyl-4-carboxylate (30)

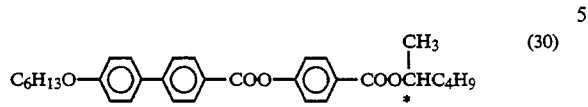

The procedure in 4) of Example 5 was followed except that 1.2 g of the compound (19) in Example 5 was replaced with 1.1 g of the compound (29). There resulted 0.8 g of a final compound (30).

A series of phases of the compound (30) are as follows. There was no antiferroelectric phase.

Comparative Example 5

1) Preparation of 4-(4′-n-hexadecanoxy)-biphenylcarboxylic Acid (31)

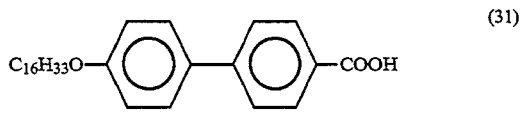

The procedure in 1) of Example 5 was followed except that 13.0 g of n-heptyl bromide was replaced with 2.1 g of n-hexadecyl bromide. There resulted 16.4 g of a final compound (31).

2) Preparation of 4-(1-methylpentyloxycarbonylphenyl)-4′-n-hexadecanoxybiphenyl-4-carboxylate (32)

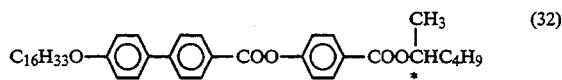

The procedure in 4) of Example 5 was followed except that 1.2 g of the compound (19) was replaced with 1.45 g of the compound (31). There resulted 1.0 g of a final compound (32).

A series of phases of the compound (32) are as follows. There was no antiferroelectric phase.

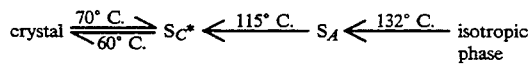

Example 9

1) Preparation of 4-(4′-n-octyloxy)biphenylcarboxylic Acid (1)

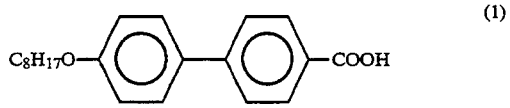

The procedure in 1) of Example 1 was repeated to obtain the final compound (1).

2) Preparation of 4-acetoxy-1-(1-methylnonyloxy)benzene (33)

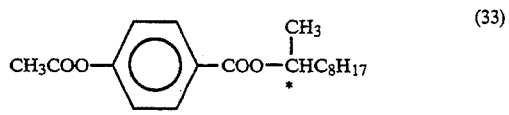

4-Acetoxybenzoic acid (3.5 g) was added to 25 ml of thionyl chloride, and the reaction was run under reflux for 10 hours. After excess thionyl chloride was evaporated, 10 ml of pyridine and 50 ml of toluene were added, and 2.0 g of optically active S-(+)-2-decanol was added dropwise. After the addition, the resulting mixture was heated under reflux for 4 hours, left to cool and diluted with 500 ml of chloroform. The organic layer was washed with dilute hydrochloric acid, a 1N sodium hydroxide aqueous solution and water in this order and dried with magnesium sulfate. Further, the solvent was evaporated to obtain 1.8 g of a final crude compound (33).

3) Preparation of 4-hydroxy-1-(1-methylxoycarbonyl)benzene (34)

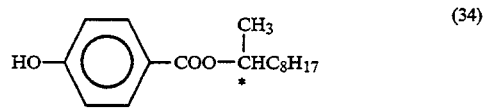

The crude compound (33) (1.8 g) was dissolved in 50 ml of ethanol, and 4 g of benzylamine was added dropwise. The mixture was stirred at room temperature for 4 hours, diluted with 500 ml of chloroform, washed with dilute hydrochloric acid and water in this order and dried with magnesium sulfate. After the solvent was evaporated, the residue was subjected to isolation and purification by silica gel column chromatography. There was obtained 1.4 g of a final compound (34).

(4) Preparation of 4-(1-methylnonyloxycarbonylphenyl)-4′-n-octyloxybiphenyl-4-carboxylate (35)

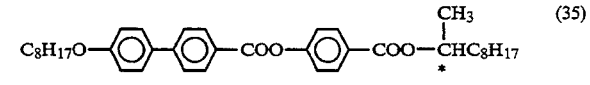

To 1.0 g of the compound (1) was added 10 ml of thionyl chloride, and the mixture was heated under reflux for 10 hours. After excess thionyl chloride was evaporated, 10 ml of pyridine and 60 ml of toluene were added, and 20 ml of a toluene solution containing 0.5 g of the compound (34) was added dropwise, followed by the reaction at room temperature for 10 hours. After the reaction, the reaction mixture was diluted with 500 ml of chloroform, and washed with dilute hydrochloric acid, a 1N sodium hydroxide aqueous solution and water in this order. The organic layer was dried with magnesium sulfate. After the solvent was evaporated, the residue was subjected to isolation by silica gel column chromatography. The resulting product was then recrystallized from ethanol to obtain 0.8 g of a final compound (35).

Figure 16:
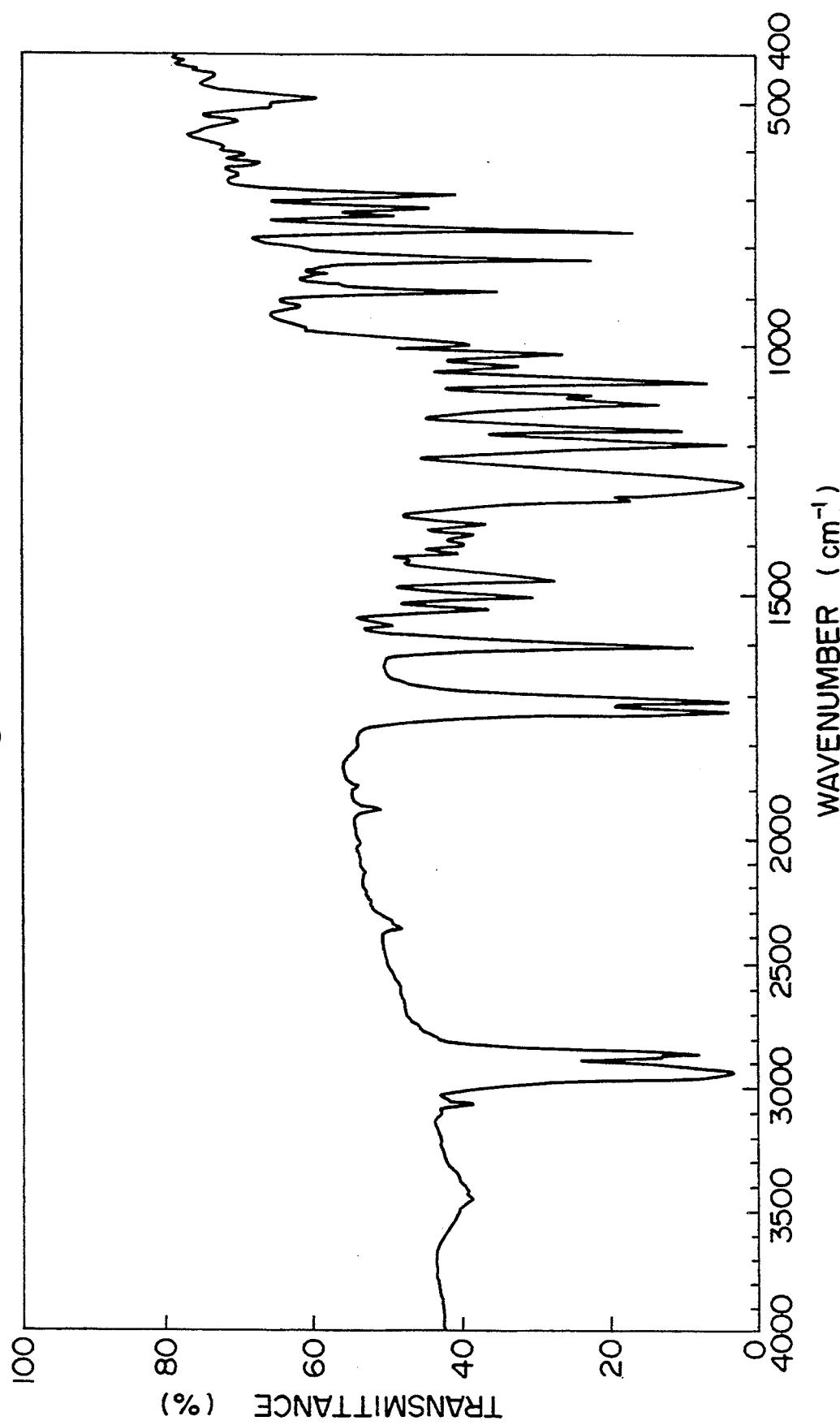
FIG. 16 is an infrared absorption spectrum of the liquid crystal compound (35).

An infrared absorption spectrum of the final compound (35) is shown in FIG. 16. Identification of phases was carried out by observation of a texture and measurement by DSC.

Phase transition temperatures of the compound (35) are as follows.

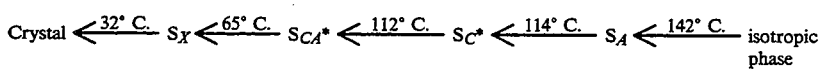

Figure 15:
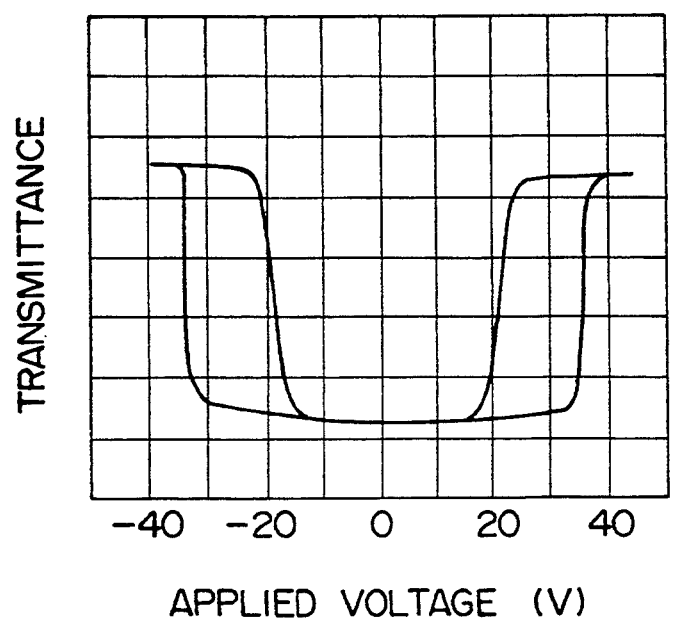
FIG. 15 shows an optical response hysteresis of a liquid crystal compound (35) in this invention which will be later described in Examples.

5) Identification of the antiferroelectric phase of the compound (35) was conducted in the same way as in 5) of Example 1. A double hysteresis peculiar to the antiferroelectric phase was observed in a temperature region of from 109° C. to 60° C. An optical response hysteresis at 70° C. is shown in FIG. 15.

Examples 10 to 15

In the same way as in Example 9, liquid crystal compounds represented by formula

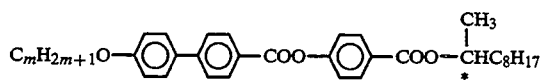

wherein m is 7, 9, 10, 11, 12 and 14, were prepared, and identification of phases was carried out by observation of a texture and measurement by DSC.

Phase transition temperatures of these compounds are shown in Table 1. Said Table 1 revealed that all these compounds had the antiferroelectric phase.

The optical response of said liquid crystal compounds was measured in the same way as in 5) of Example 1, and a double hysteresis peculiar to the antiferro electric phase was observed.

TABLE 1

Phase transition temperatures of compounds represented by formula

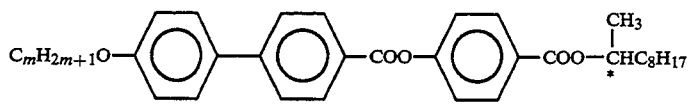

| Example No. | m | Phase transition temperature |
|---|---|---|
| 10 | 7 | crystal ⇌ 56° C. SCA* ⇌ 99° C. SA ⇌ 132° C. isotropic phase |
| 11 | 9 | crystal ⇌ 8.7° C. SX ⇌ 50° C. SCA* ⇌ 99° C. SC* ⇌ 104° C. SA ⇌ 130° C. isotropic phase |
| 12 | 10 | crystal ⇌ 7.4° C. SX ⇌ 37° C. SCA* ⇌ 102° C. SC* ⇌ 109° C. SA ⇌ 119° C. isotropic phase |
| 13 | 11 | crystal ⇌ 26° C. SCA* ⇌ 92° C. SC* ⇌ 118° C. SA ⇌ 128° C. isotropic phase |
| 14 | 12 | crystal ⇌ 34° C. SCA* ⇌ 84° C. SC* ⇌ 116° C. SA ⇌ 123° C. isotropic phase |
| 15 | 14 | crystal ⇌ 60° C. SCA* ⇌ 77° C. SC* ⇌ 119° C. SA ⇌ 125° C. isotropic phase |

SX is an unidentified smectic phase.

Comparative Examples 6 and 7

In the same way as in Example 9, liquid crystal compounds represented by formula

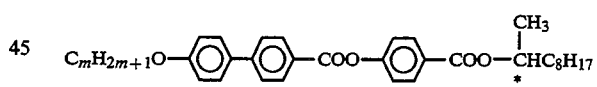

wherein m is 6 or 16, were prepared, and identification of phases was carried out by observation of a texture and measurement by DSC. The results are shown in Table 2. None of these liquid crystal compounds had the antiferroelectric phase.

TABLE 2

Phase transition temperatures of compounds represented by formula

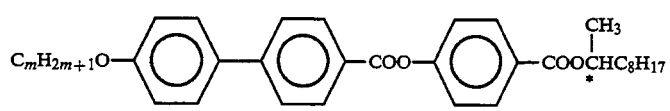

| Comparative Example No. | m | Phase transition temperature |
|---|---|---|
| 6 | 6 | crystal ⇌ 61° C. SA ⇌ 148° C. isotropic phase |
| 7 | 16 | crystal ⇌ 59° C. SC* ⇌ 118° C. SA ⇌ 133° C. isotropic phase |

What is claimed is:

1. A liquid crystal compound represented by formula (I),

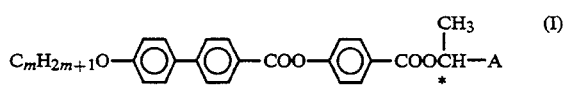

wherein A represents —C$_3$H$_7$, —C$_4$H$_9$ or —C$_8$H$_{17}$; when A is —C$_3$H$_7$, m is an integer of 8, 10, 12 or 14; and when A is —C$_4$H$_9$, m is an integer of 8, 10, 12 or 14 and when A is —C$_8$H$_{17}$, m is an integer of 7, 8, 9, 10, 11, 12, or 14, said compound having an antiferroelectric phase.

2. The liquid crystal compound of claim 1 represented by formula (I-a)

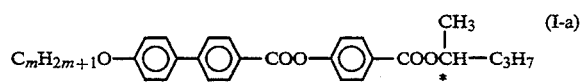

wherein m is an integer of 8, 10, 12 of 14.

3. The liquid crystal compound of claim 1 represented by formula (I-b)

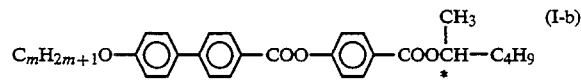

wherein m is an integer of 7, 8, 12 or 14.

4. The liquid crystal compound of claim 1 represented by formula (I-c)

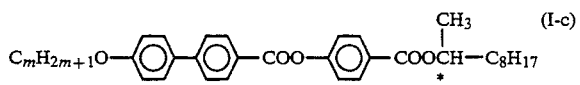

wherein m is an integer of 7, 8, 9, 10, 11, 12 or 14.

5. The liquid crystal compound of claim 1 which is at least one compound selected from the group consisting of compounds represented by formulas:

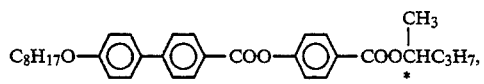

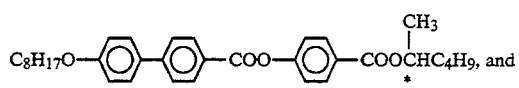

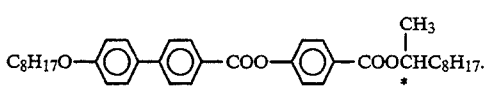

6. A liquid crystal display device containing the liquid crystal compound of formula (I) recited in claim 1 as a liquid crystal component.

7. The liquid crystal display device according to claim 6, wherein the liquid crystal compound of formula (I) is at least one compound represented by the formulas

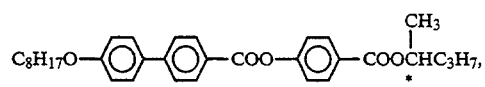

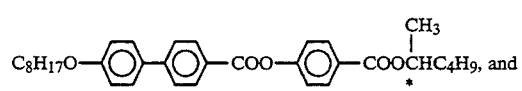

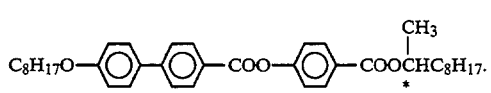

* * * * *